(12) United States Patent
Hendriks et al.

(10) Patent No.: US 7,645,824 B2
(45) Date of Patent: *Jan. 12, 2010

(54) COLOR STABLE ANTIMICROBIAL COATINGS

(75) Inventors: Eugene P. Hendriks, Westford, MA (US); Jeffrey A. Trogolo, Boston, MA (US)

(73) Assignee: Agion Technologies, Inc, Wakefield, MA (US)

( * ) Notice: Subject to any disclaimer, the term of this patent is extended or adjusted under 35 U.S.C. 154(b) by 740 days.

This patent is subject to a terminal disclaimer.

(21) Appl. No.: 11/337,760

(22) Filed: Jan. 23, 2006

(65) Prior Publication Data

US 2006/0156948 A1   Jul. 20, 2006

Related U.S. Application Data

(63) Continuation-in-part of application No. 10/875,451, filed on Jun. 24, 2004.

(51) Int. Cl.
*C08K 3/10* (2006.01)
*C08K 3/22* (2006.01)

(52) U.S. Cl. .................. 524/403; 524/413; 523/122

(58) Field of Classification Search .............. 524/403, 524/413; 523/122
See application file for complete search history.

(56) References Cited

U.S. PATENT DOCUMENTS

| | | | |
|---|---|---|---|
| 4,938,958 A | 7/1990 | Niira et al. | |
| 5,334,388 A | 8/1994 | Hoang et al. | |
| 5,698,229 A | 12/1997 | Ohsumi et al. | |
| 6,093,407 A | 7/2000 | Cummings et al. | |
| 6,432,416 B1 | 8/2002 | Cummings et al. | |
| 6,436,422 B1 | 8/2002 | Trogolo et al. | |
| 6,585,989 B2 | 7/2003 | Herbst et al. | |
| 6,734,157 B2 | 5/2004 | Radwanski et al. | |
| 6,866,859 B2 | 3/2005 | Trogolo et al. | |
| 6,946,433 B2 | 9/2005 | Green et al. | |
| 2002/0068093 A1 * | 6/2002 | Trogolo et al. | .............. 424/618 |
| 2003/0118664 A1 | 6/2003 | Trogolo et al. | |
| 2005/0035327 A1 | 2/2005 | Canada et al. | |
| 2005/0037057 A1 | 2/2005 | Schuette et al. | |
| 2005/0037680 A1 | 2/2005 | Canada et al. | |
| 2005/0064020 A1 | 3/2005 | Schuette et al. | |
| 2005/0080158 A1 | 4/2005 | Ong et al. | |
| 2005/0136100 A1 | 6/2005 | Foss | |
| 2005/0147657 A1 | 7/2005 | Canada et al. | |

FOREIGN PATENT DOCUMENTS

| | | |
|---|---|---|
| EP | 0781566 | 2/1997 |
| JP | 4050367 | 2/1992 |
| JP | 4050368 | 2/1992 |
| JP | 09100205 | 4/1997 |
| JP | 11012476 | 1/1999 |

OTHER PUBLICATIONS

AgION Technologies, CleneCoat® Epoxy Coating System Data Sheet (Apr. 2004).
AgION Technologies, CleneCoat® Epoxy Coating System Data Sheet (Apr. 2004)The Value of Clean(TM) Solutio.

* cited by examiner

*Primary Examiner*—Kriellion A Sanders
(74) *Attorney, Agent, or Firm*—Edward K Welch, II; IP & L Solutions

(57) ABSTRACT

The present invention provides for a color stable antimicrobial coatings and coating systems comprising a silver ion-exchange type antimicrobial agent. In particular, coatings and coating systems having little, if any, discoloration are provided with no loss of antimicrobial efficacy.

20 Claims, 1 Drawing Sheet ns/**

COLOR STABLE ANTIMICROBIAL COATINGS

Figure 1:
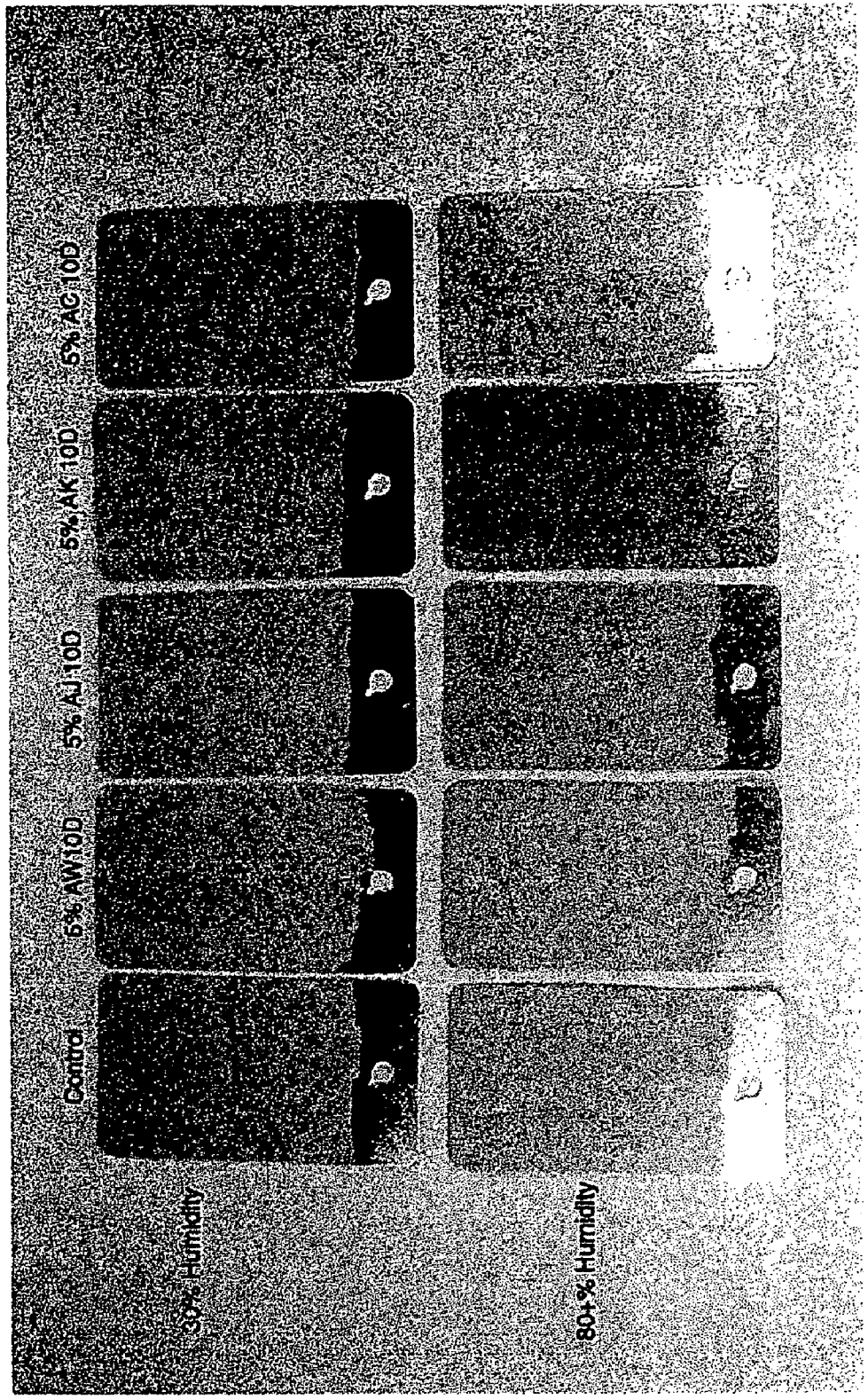

This application is a continuation-in-part of co-pending U.S. patent application Ser. No. 10/875,451, filed Jun. 24, 2004, and entitled "Antimicrobial Coating for Erosive Environments", the contents of which are incorporated herein by reference.

FIELD OF THE INVENTION

The present invention relates to ionic silver based antimicrobial coatings, especially erosive coatings, having improved color stability without compromising on the level of antimicrobial active silver. In particular, the present invention is directed towards antimicrobial coatings containing ion-exchange type antimicrobial agents, especially zeolites, having excellent antimicrobial properties without discoloration due to the formation of silver compounds.

BACKGROUND OF THE INVENTION

The antimicrobial properties of a number of inorganic materials, especially metals such as silver, copper, zinc, mercury, tin, gold, lead, bismuth, cadmium, chromium and thallium, have long been known. Certain of these metals, especially silver, zinc, gold and copper, have enjoyed greater success due to their relatively low environmental and toxicological effects and high antimicrobial activity. More recently, antimicrobial agents which incorporate ionic forms of these metals, especially through an ion-exchange type mechanism, have achieved greater attention due to the higher bioactivity of the ionic versus the metallic form of these metals in an antimicrobial application. Exemplary ion-exchange type antimicrobial agents include those wherein the ion-exchange carrier particles are ceramic particles including zeolites, hydroxy apatites, zirconium phosphates and the like. Antimicrobial agents based on zeolite carriers are disclosed in, for example, U.S. Pat. Nos. 4,911,898; 4,911,899; 4,938,955; 4,906,464; and 4,775,585. Antimicrobial zirconium phosphates include those disclosed in, for example, U.S. Pat. Nos. 4,025,608 and 4,059,679 and the Journal of Antibacterial Antifungal Agents Vol. 22, No. 10, pp. 595-601, 1994. Finally, antimicrobial hydroxyapatites powders include those disclosed in U.S. Pat. Nos. 5,009,898 and 5,268,174, among others.

Despite the relative, though restrained, success of these antimicrobial agents as additives for polymer resins and the several patent publications teaching or suggesting their utility in coatings, these antimicrobial agents have actually found limited commercial utility in coating applications. Though, as noted below, the problems associated with their use are common to both coating and molding/compounding applications, the impact is far greater on coating applications; especially since coating applications are more visible and, indeed, are intended to provide a decorative or esthetic appearance to the substrate being coated.

The first significant problem associated with ion-exchange type antimicrobial agents is the fact that, in non-hydrophilic compositions, only that amount of the antimicrobial agent which is present at or proximate to, on a molecular scale, the surface of the polymer substrate or coating actually participates in providing antimicrobial activity. This inactivity arises from the fact that these antimicrobial agents rely upon an ion-exchange mechanism that is facilitated by, if not reliant upon, the presence of water or a similar medium, especially an aqueous based or containing medium, which transports the exchange cations in and the antimicrobial metal cations out of the ceramic particles. Non-hydrophilic polymers do not possess the internal moisture or water needed for this transport and, consequently, those antimicrobial particles that lie below the surface are inactive: at least until they become exposed due to wear and/or erosion.

Perhaps the more significant problem associated with ion-exchange type antimicrobial agents is their tendency to cause discoloration of the polymer resin or coating composition into which they are incorporated. In polymer compounding applications discoloration is often immediate; arising from an interaction of silver, especially silver ions on the surface of the particles and/or exchanging out of the particles (due to the presence of moisture in the compound pre-mix or the air), with other compounds, ions, and the like present in the polymer and/or the compound pre-mix into which the antimicrobial agent is being incorporated, particularly when conducted in the presence of moisture, including conditions of high humidity. Whether immediate or not, whether in a compounded polymer or polymer coating, discoloration also manifests itself over time as a result of the occurrence of the aforesaid interaction between the silver and other reactive components during compounding or cure, as appropriate, and/or as a result of various environmental conditions, especially high humidity and/or UV light, acting upon the so-formed silver compounds. While the use of these antimicrobial agents in polymer resins can be directed to articles or components that are not readily visible, coatings by design are intended for visual impact. Thus, discoloration is of utmost concern with coatings.

Numerous efforts have been undertaken to improve the use of ion-exchange type antimicrobial agents in coatings and polymer compositions. So far, such efforts have found limited success: oftentimes achieving success relative to one issue, but not both issues. For example, in U.S. Pat. No. 6,436,422, Trogolo et. al., employed hydrophilic polymer coatings so as to ensure that all of the antimicrobial agent within the coating was active and participating in providing antimicrobial efficacy. However, hydrophilic polymers, whether as a coating or molded material, have limited use due to their severely limited physical and performance properties. Furthermore, discoloration persisted.

Alternatively, where efforts have been made to address both issues, they were addressed only to a limited extent. For example, subsequent developments by Trogolo et. al., (see e.g., US 2003-0118664) achieved some, though limited success against both issues. Specifically, Trogolo et. al. found that by encapsulating the antimicrobial particles in a hydrophilic polymer they were able to increase the effective particle size of the antimicrobial agent, thereby increasing the likelihood that any given antimicrobial particle would be present at or proximate to the surface of the polymer substrate or coating into which it is incorporated. These antimicrobial additives also had the benefit of slowing down, if not reducing, discoloration since the hydrophilic polymer encapsulating material essentially isolated the antimicrobial active from the polymer resin or coating materials into which it was being incorporated during the critical compounding process. Furthermore, what little, if any, interaction or reaction that did take place was essentially limited to taking place in the encapsulating material and did not transition into the polymer matrix itself. Though the encapsulated additives of Trogolo et. al. provide many benefits, there are still lingering concerns with, among other issues, the introduction of yet another ingredient, the hydrophilic polymer, into the matrix polymer composition to be rendered antimicrobial; the affinity or incompatibility of the hydrophilic polymer with the matrix polymer; inactive particles in thick molded parts or coating applications; and long-term discoloration arising from the subsequent release of the antimicrobial ions from the antimicrobial additive particles themselves into or at the interface with the matrix polymer.

Generally speaking, it can be seen that antimicrobial coating systems require a compromise amongst several desirable properties. Hydrophilic polymer coatings are especially suited for use with ion-exchange type antimicrobial agents; however, these coatings are typically easily abraded in any erosive environment and do not give lasting protection. Non-hydrophilic polymers provide improved wear resistance due to their stronger physical performance characteristics and properties but suffer, comparatively, in terms of their antimicrobial activity. These problems can be exacerbated by surfactants and leveling agents commonly used in coating systems and designed to form a skin at the surface of the coating to control surface finish. This same skin can also form over the antimicrobial agent; thereby potentially inactivating the same. Generally this skinning effect results from two circumstances. The first is where the particle is suspended in the coating and the coating forms a film over the surface of the particle even though the particle is at or proximate to the surface of the top coat. The second is where the coating is such that even where the antimicrobial particles protrude above the surface of the coating matrix (as for example where the particles have a greater diameter than the thickness of the coating), the surface tension forces of the coating are such that it still forms a film over the particles. Although greater amounts of the antimicrobial agent will provide a higher concentration of the antimicrobial agent at the surface; this is more costly and increases the likelihood of discoloration since the polymer system has even more silver content.

Because silver based antimicrobial coatings, especially those involving silver salts and/or ionic silver, are especially prone to discoloration, especially over time, their utility is severely limited to those applications which have short life expectancies and/or are not readily visible or, if visible, are not employed where color stability and esthetics are important.

Thus, there remains a need to provide a silver based antimicrobial coating in a form that is suitable to impart antimicrobial properties without the accompanying problems of the prior art. More specifically, there remains a need to provide a silver based antimicrobial coating that provides good long-term antimicrobial activity and color stability.

SUMMARY OF THE INVENTION

This invention provides for antimicrobial coating compositions and systems wherein the antimicrobial agent is an ion-exchange type antimicrobial agent having a combination of silver and copper ions ion-exchanged thereon. The coatings may be single or multi-part coating compositions that are applied as a single layer or multiple layers, especially multi-layered erosive coatings. The coating composition, in the case of single layer coatings, or the base coat composition, in the case of the multilayered coatings coat contains a silver-copper ion-exchange type antimicrobial agent and is preferably a highly durable material.

In the case of multilayered coating systems, a top coat is placed over the base coat and typically comprises a hydrophilic polymer and an antimicrobial agent, most preferably a silver-copper ion-exchange type antimicrobial agent. Alternatively, the top coat polymer is non-hydrophilic and the top coat thickness is, at most, slightly thicker, but is preferably about the same thickness as or thinner than the average diameter particle size of the antimicrobial agent or the top coat is of such a composition as does not facilitate skinning of the antimicrobial agent.

The coating compositions of the present invention may be colored or clear and may be transparent, translucent or solid when cured. Though there may be a slight discoloration, oftentimes a bluish hue, in white and whitish coatings, these coatings have essentially none of the discoloration associated with the same coating formulations which employ a comparable silver ion based antimicrobial agent having the same silver ion content but without the copper ions. Besides the unexpected effect on discoloration, the presence of copper ions also introduces antifungal properties to the coating formulations, a property not typically associated with silver-only based antimicrobial agents.

The coating compositions according to the present invention may be applied to most any substrate or surface, especially exposed surfaces. Due to their enhanced color stability, these coating compositions are particularly suited for use in decorative and/or aesthetic coating applications. As such, these coatings are especially suitable for use on walls, floors, ceilings and other building surfaces, especially work and/or touch surfaces.

DETAILED DESCRIPTION OF THE DRAWINGS

FIG. 1 is a photograph of two comparative series of stock plates coated with coatings in accordance with and outside the scope of the present invention.

DETAILED DESCRIPTION OF THE INVENTION

All patent applications, patents, patent publications, and literature references cited in this specification, whether referenced as such, are hereby incorporated by reference in their entirety. In the case of inconsistencies, the present description, including definitions, is intended to control.

The present invention provides for curable antimicrobial coating compositions and system having good long-term color stability as well as antimicrobial efficacy. When used herein and in the appended claims, the terms "curable", "cure" or "set" refer to the ability or the act of transformation of a liquid or a flowable 100% solids coating composition to a solid, finished coating. Most often reference to cure or cured will be in relation to traditional thermoset or cross-linkable coating compositions. However, these terms as well as the term "set" are also used in relation to those coatings that form through solvent evaporation or a combination thereof with cross-linking. Preferably, though, the coatings cure by other than UV radiation and are free of photoinitiators. Similarly, as used herein and the appended claims, color stability refers to the ability of the coating compositions to exhibit no or little change in color due to the presence of the antimicrobial additive and, in any event, markedly less discoloration as compared to similar compositions using the same ceramic carrier particles with the same amount of silver ions but no copper ions.

The coating compositions or systems according to the practice of the present invention may be single part or multi-part compositions that are applied as a single layer or in multiple layers to a given substrate. Typical single part compositions are 100% solids or "solvent" based systems such as true solutions, dispersions or colloids. 100% solid compositions include powder coatings as well as flowable 100% solids curable compositions. Generally, these compositions cure or set upon exposure to the atmosphere or other curing conditions. Multipart compositions comprise two or more parts that are essentially shelf stable as long as the two parts remain isolated from one another but cure or become curable upon mixing of the two or more parts.

The present invention is also applicable to coating systems that comprise one or more coating layers, each layer of which may have originated from a single or multi-part coating composition. Especially preferred multilayered coating systems are erosive coating systems comprising a strong base coat and a readily errodable top coat, particularly hydrophilic top coats.

The chemistry or formulation of the coating compositions vary widely and are selected based on the desired physical properties of the coating compositions, the mode of application (e.g., solution based, curable 100% solids or powder coating), the pot life (if applicable) and the environmental conditions to which they are exposed in use. Typically, in the case of thermoset coatings the choice of polymer or polymerizable components is based on the cure method and pot life as well as the adhesion, wear, and appearance characteristics or properties. In the case of thermoplastic coatings, selection of the thermoplastic polymer is based on the solvent needed and/or the ease of application, especially as powder coatings, as well as their adhesion, wear and appearance characteristics or properties. For high wear or stress environments or applications, it is preferred that the coatings be non-hydrophilic. However, for other applications, especially where it is desired to have a coating of a defined life as in the case of the top coat of a multilayered coating system, especially an erosive coating system, it is preferred that the coating be a hydrophilic coating.

Suitable thermoplastic polymers include, but are not limited to, polypropylene, polyethylene, polystyrene, ABS, SAN, polybutylene terephthalate, polyethylene terephthalate, nylon 6, nylon 6,6, nylon 4,6, nylon 12, polyvinylchloride, polyurethanes, silicone polymers, polycarbonates, polyphenylene ethers, polyamides, polyethylene vinyl acetate, polyethylene ethyl acrylate, polylactic acid, polysaccharides, polytetrafluoroethylene, polyimides, polysulfones, and a variety of other thermoplastic polymers and copolymers. Suitable thermoset or cross-linkable coatings include, but are not limited to, phenolic resins, urea resins, epoxy resins, including epoxy-novalak resins, polyesters, epoxy polyesters, acrylics, acrylic and methacrylic esters, polyurethanes, acrylic or urethane fortified waxes and a variety of other thermoset or thermosettable polymers and copolymers. Especially preferred thermoset coating systems are those based on epoxy resins, whether 100% solids or aqueous dispersions/latexes, due to their excellent adhesion to a variety of substrates and durability. Suitable epoxy resin systems include those sold by Corro-Shield of Rosemont, Ill. as well as Burke Industrial Coatings of Vancouver, Wash.

As noted previously, coatings produced in accordance with the teaching of the present invention may comprise a single layer or two or more layers, each of which incorporates one or more antimicrobial agents. Single layer coatings are preferred due to their simplicity of application; however, as noted above, most coating applications do not allow for the use of hydrophilic polymers and, therefore, there is concern for antimicrobial agents contained within the coating and below the surface thereof. This concern may only be temporary in the case of coated surfaces that are subject to wear during use, especially floors. Alternatively, even those coatings, as well as all non-hydrophilic coatings where skinning over is a concern, can be activated by quickly eroding the surface layer of polymer coating. Depending upon the physical properties of the coatings, such may be achieved simply by buffing and/or lightly sanding the surface. Yet another alternative would be to employ hydrophilic polymer encapsulated antimicrobial agents, as discussed further below.

Where both immediate antimicrobial activity and high strength, durable coatings are needed or desirable, it is especially preferred to employ multi-layered coatings, especially erosive coatings wherein the desired performance capable coating is applied as a base layer and a comparatively readily errodable antimicrobial top coat, especially an antimicrobial hydrophilic top coat, is applied over the base layer. As discussed more explicitly in the parent application, U.S. Ser. No. 10/875,451, filed Jun. 24, 2004, the top coat is designed to provide immediate release of the antimicrobial active as is and/or is readily erodable so that immediate or near immediate release of the antimicrobial active is manifested. Preferably the top coat is an antimicrobial hydrophilic top coat that allows for immediate antimicrobial activity. As the top coat is worn away, the skin coat or surface of the antimicrobial base layer is also worn away, exposing the therein contained antimicrobial agents so as to provide antimicrobial activity. As the whole of the top coat is worn away, the exposed base layer then provides the ultimately desired long wear and antimicrobial properties.

In the preferred embodiment of this aspect of the present invention, the top coat formulation comprises a hydrophilic polymer and an antimicrobial agent. Hydrophilic polymers are those that can absorb sufficient water to enable the antimicrobial agent to exhibit good antimicrobial behavior, i.e., to allow for the migration and release of the antimicrobial active agent. The polymer will be characterized by having water absorption at equilibrium of at least about 2%, preferably at least about 5%, most preferably at least about 20%, by weight as measured by ASTM D570. Especially suitable hydrophilic polymers include those having water absorption capabilities at equilibrium of from about 50% and to about 150% by weight. Typical hydrophilic polymers comprise polymer chains having a substantial quantity of monomers having polar groups associated with them, such that the overall polymeric composition is rendered hydrophilic. The polar groups can be incorporated into the polymer main chain as in for example polyesters, polyurethanes, polyethers or polyamides or the polar groups may be pendant to the main chain as in for example, polyvinyl alcohol, polyacrylic acids or as in ionomer resins such as Surlyn®. Surlyn® ionomer resins are available from Dupont and are based upon the random copolymer poly (ethylene-co-methacrylic acid) wherein some or all of the methacrylic acid units are neutralized with a suitable cation, commonly $Na^+$ or $Zn^{+2}$. While not being limited by way of theory, it is believed that the inclusion of polar groups allows water to more readily permeate the polymer and consequently, to allow transport of the metal ion through the top coat polymer layer.

As another option, the top coat can be made hydrophilic by blending a hydrophilic polymer with a non-hydrophilic polymer and/or cross-linkable coating polymer precursor. A preferred blend is made by using a supporting polymer comprising a plurality of functional moieties capable of undergoing crosslinking reactions, said supporting polymer being soluble in or emulsified in an aqueous based medium; and a hydrophilic polymer, said hydrophilic polymer being associated with the supporting polymer as described in U.S. Pat. No. 6,238,799. The ratio of the hydrophilic to non-hydrophilic and/or cross-linkable polymer depends on the hydrophilicity of the hydrophilic polymer and the desired hydrophilicity of the resultant blend.

Suitable hydrophilic polymers for use in the present invention include, for example, polyacrylates and polymethacrylates including (poly)hydroxyethyl methacrylate, (poly)hydroxypropyl methacrylate, (poly)glycerol methacrylate, copolymers of hydroxyethyl methacrylate and methacrylic acid; polyacrylamides; polymethacrylamides; hyaluronan; polysaccharides; polylactic acid; copolymers of lactic acid; (poly)vinyl pyrrolidone; polyamides such as Nylon 6,6, Nylon 4,6 and Nylon 6,12; cellulosics; polyureas; polyurethanes and certain polyesters containing a high percentage (at least about 10% by weight, preferably at least about 25% by weight or more) of polyalkylene oxide; polyvinyl acetate, polyvinyl alcohol, and copolymers of polyvinyl alcohol and polyvinylacetate, polyvinylchloride, copolymers of polyvinyl acetate and polyvinylchloride and hydroxyl-modified vinyl chloride/vinyl acetate copolymers; styrene/methacrylic acid/hydroxyethyl methacrylate copolymers, styrene/methacrylic acid/hydroxypropyl methacrylate copolymers, methyl methacrylate/methacrylic acid copolymers, ethyl methacrylate/styrene/methacrylic acid copolymers and ethyl methacrylate/-methyl methacrylate/styrene/methacrylic acid copolymers, copolymers based upon the cellulosics, and copolymers which utilize vinyl pyrrolidone monomers, among numerous others.

Preferably the hydrophilic polymer is chosen from polyacrylates and poly (meth)acrylates (especially polyhydroxyethyl methacrylate), polyacrylamide, polyvinylpyrrolidinone, polyurea, polysaccharides, polylactic acid and polyurethane. Polyurethanes containing a high percentage (at least about 10% by weight, preferably at least about 25% by weight or more) of polyalkylene oxide are especially useful in this invention. Exemplary hydrophilic polymers include TECOPHILIC® polyurethanes sold by Thermedics of Woburn, Mass.; AEP Polymers from I H Polymeric Products of Kent, England; and the (meth)acrylic ester based coatings from Surface Solutions Laboratories, Inc. of Carlisle, Mass.

In multi-layered coating systems, especially two-layered erosive systems, it is not necessary that the top coat be a hydrophilic material. For example, top coats employing a higher concentration of the antimicrobial agent and/or encapsulated antimicrobial agents may be employed to increase the amount of such agents at the surface. Alternatively, the thickness of the top coat may be regulated relative to the average particle size of the antimicrobial additive to ensure that at least a portion of the antimicrobial particles are at the surface or the surface may be dusted with the antimicrobial agent prior to cure of the top coat. Additionally, as noted previously, the cured top coat may be subjected to a mild abrading to expose the skinned over antimicrobial agent. In the latter case, the non-hydrophilic top coat is typically of a material that is less durable than the underlying base coat material. These non-hydrophilic top coats may be thermoset (crosslinkable) or thermoplastic and may comprise non-hydrophilic species of the aforementioned hydrophilic polymers, such as, for example, epoxy coating compositions.

The selection of the top coat and base coat formulations to be used in any single multi-layered application should be such that each layer is compatible with the other. The key aspect of compatibility, in this respect, is the adhesion between the layers. If there is insufficient peel strength or adhesive strength between the layers, the top coat may slough off prematurely, before antimicrobial agent in the base coat is exposed. Those skilled in the art will readily recognize, based on the compositions of each, whether compatibility is or will be an issue. For example, typically one would not place an oil-based top coat on a water-based latex base coat. Alternatively, one could prepare simple test pieces with the intended combination of top coat and base coat and evaluate the integrity of the bond between the two coatings. Yet another alternative may be the use of an adhesion promoting primer between the two coating layers.

Antimicrobial agents suitable for use in the practice of the present invention comprise ion-exchange type ceramic particles having both ion-exchanged copper and silver ions which impart antimicrobial activity to the coating. Exemplary ion-exchange ceramic particles include, but are not limited to zeolites, hydroxyapatite, zirconium phosphates and other ion-exchange ceramics. Hydroxyapatite particles containing antimicrobial metals are described in, e.g., U.S. Pat. Nos. 5,009,898 and 5,268,174. Zirconium phosphates containing antimicrobial metals are described in, e.g., U.S. Pat. Nos. 4,025,608; 4,059,679; 5,296,238; 5,441,717 and 5,405,644 as well as in the Journal of Antibacterial and Antifungal Agents, Vol. 22, No. 10, pp. 595-601, 1994. Antimicrobial zeolites containing ion-exchanged antimicrobial metal ions are described in, eg., U.S. Pat. Nos. 4,911,898; 4,911,899; 4,938,955; 4,938,958; 4,906,464; and 4,775,585.

Generally speaking, the antimicrobial agents used in the practice of the present invention are prepared by an ion-exchange reaction in which non-antimicrobial ions present in the ceramic particles, for example sodium ions, calcium ions, potassium ions and iron ions in the case of zeolites, are partially or wholly replaced with the antimicrobial copper and silver ions. The combined weight of the antimicrobial metal ions will be in the range of from about 0.1 to about 35 wt %, preferably from about 2 to 25 wt %, most preferably from about 4 to about 20 wt % of the ceramic particle based upon 100% total weight of ceramic particle wherein the weight ratio of silver to copper ions is from 1:10 to 10:1, preferably from 5:1 to 1:5, most preferably from 2.5: to 1:2.5. In particular each antimicrobial metal ion may be present in the range of from about 0.1 to about 25 wt %, preferably from about 0.3 to about 15 wt %, most preferably from about 2 to about 10 wt % of the ceramic particle based on 100% total weight of the ceramic particle. In an especially preferred embodiment, the ceramic particle contains from about 0.3 to about 15 wt % of silver ions and from about 0.3 to about 15 wt % of copper ions in a weight ratio of 5:1 to 1:5.

In addition to the copper and silver ions, the antimicrobial ceramic particles may also have other antimicrobial metal ions such as zinc ions. If present these additional antimicrobial metal ions will be present in the ranges set forth above for the silver and copper ions and will be included in the total weight of antimicrobial metal ions also mentioned above.

In the preferred embodiments of the present invention the antimicrobial ceramic particles are zeolites, especially those of the type described in U.S. Pat. Nos. 4,911,898; 4,911,899 and 4,938,958. Suitable zeolites include natural and synthetic zeolites. "Zeolite" is an aluminosilicate having a three dimensional skeletal structure that is represented by the formula: $XM_{2/n}O$—$Al_2O_3$—$YSiO_2$-$ZH_2O$ wherein M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. Typically the surface area of these zeolites is at least 150 $m^2$/g (anhydrous zeolite as standard) and the $SiO_2/Al_2O_3$ mole ratio is preferably less than 14 and more preferably less than 11. The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite=11.5 meq/g; mordenite=2.6 meq/g; analcite=5 meq/g; clinoptilolite=2.6 meq/g; chabazite=5 meq/g;

and erionite=3.8 meq/g. The present invention is not, however, limited to the foregoing zeolites.

The antimicrobial metal ions used in the antimicrobial zeolites should be retained in and on the zeolite particles through an ion-exchange reaction. Antimicrobial zeolites in which the antimicrobial metal ions are solely or predominately adsorbed or attached without an ion-exchange reaction typically exhibit an overall decreased bactericidal effect and their antimicrobial effect is not long lasting. Nevertheless, it can be advantageous for imparting quick antimicrobial action to maintain a sufficient amount of surface adsorbed metal ion in addition to the ion-exchanged metal ion. The same is true for the other antimicrobial agents within the scope of the present invention.

The antimicrobial zeolites, as well as other antimicrobial ceramic particles, may also contain an additional discoloration agent. Preferably, the discoloration agent is biocompatible. Preferred discoloration agents include, but are not limited to, inorganic discoloration inhibitors such as ammonium. More preferably, the inorganic discoloration inhibitor is an ion-exchanged ammonium ion in the zeolite. The ammonium ions, if present, will be present in an amount of up to about 20 wt % of the ceramic particle though it is preferred to limit the content of ammonium ions to from about 0.1 to about 2.5 wt %, more preferably from about 0.25 to about 2.0 wt %, and most preferably from 0.5 to about 1.5 wt % of the ceramic particle.

A preferred antimicrobial zeolite for use in the invention is type A zeolite containing ion-exchanged silver and copper ions and is commercially available from AgION Technologies, Inc. (Wakefield, Mass., USA) under AgION trademark as AgION AC10D. This antimicrobial zeolite has approximately 3.5% by wt silver ions and 6.0% by wt. copper ions and has a mean average diameter of about 3μ.

As mentioned earlier, the antimicrobial agents employed in the practice of the present invention may also be present in the form of discrete particles of a hydrophilic polymer having encapsulated therein the antimicrobial agent. Such materials are described in United States Published Patent Application No. US2003-0118664 A1 (U.S. Ser. No. 10/032,372 filed Dec. 21, 2001 by Trogolo et al.), which is incorporated herein by reference. Suitable hydrophilic materials are the same as described above for use as the hydrophilic coating or top coat. These encapsulated antimicrobial agents are especially desired for use in non-hydrophilic coatings and coating systems as well as in multi-layered coatings where the encapsulated antimicrobial agent is preferably in the base coat, though it may be used in either or both the top coat and the base coat. Generally speaking, the encapsulated antimicrobial agent is in the form of microcapsules or particles that comprise either a single antimicrobial ceramic particle coated with or, most preferably, a plurality (several to several hundred or more) of particles of the antimicrobial agent encapsulated within a hydrophilic polymer. The particles of the encapsulated antimicrobial agent may be of many shapes and may deform somewhat during processing of the coating. Typically, the encapsulated antimicrobial agent will be in the form of spherical or ellipsoid particles having a low aspect ratio, for example, on the order of from 1 to about 4, preferably from 1 to about 2, most preferably from 1 to about 1.5 and an average diameter of 2000μ or less, preferably 1000μ or less. However, it is also contemplated that microcapsules may be of a high aspect ratio as taught in United States Published Patent Application No. US2003-0118658 A1 (U.S. Ser. No. 10/032,370 filed Dec. 21, 2001 by Trogolo et al), also incorporated herein by reference. These high aspect ratio microcapsules are typically in the shape of flakes and fibers whose aspect ratio is up to 100 or more, but typically is less than about 30.

In accordance with the practice of the present invention, the coating, or the base coat in the case of multilayered coatings, will generally contain from about 1 to about 30%, preferably from about 5 to about 20% and most preferably from about 5 to about 10%, by weight of the antimicrobial agent based on the total weight of cured coating, i.e., the solids. The foregoing ranges also hold true for the encapsulated antimicrobial agents except that the weight percent of the antimicrobial agent is based on the weight of just the antimicrobial agent exclusive of the encapsulant, i.e., the encapsulating matrix or coating, as appropriate.

In the case of multi-layered coatings, especially erosive coatings, the upper and/or top coat compositions will generally contain from about 1 to about 30%, preferably from about 5 to about 20%, and most preferably from about 5 to about 10%, by weight of the antimicrobial agent based on the total weight of the cured top coat, i.e., the solids. The foregoing ranges also hold true for the encapsulated antimicrobial agents except that the weight percent of the antimicrobial agent is based on the weight of just the antimicrobial agent exclusive of the encapsulation material.

Additionally, the aforementioned antimicrobial agents may be used alone or in combination with another antimicrobial agent and/or another pesticide agent, such as a fungicide, preferably other than silver based ion-exchange type antimicrobial agents having a silver ion content of greater than 1% by weight. Suitable supplemental agents include various known organic antimicrobial agents including, e.g., antimicrobial quaternary ammonium, phosphonium and/or sulfonium salts and compounds, including those disclosed in Konagaya et. al., U.S. Pat. No. 6,013,275, which is incorporated herein by reference, as well as triclosan. Alternatively, the supplemental antimicrobial or pesticide agent may be based on antimicrobial and/or antifungal metals, of the type first mentioned above, and may be present in the form of the metal itself or simple salts thereof or as low molecular weight organometallic compounds. Such materials include the oxides, sulfides, chlorides, bromides, carbonates, nitrates, phosphates, dihydrogen phosphates, sulfates, oxalates, acetates, benzoates, thiosulfates and the like of such antimicrobial metals. Specific examples include silver nitrate, cupric oxide, zinc acetate; zinc oxide and copper-8 quinolinolate. Alternatively, the supplemental antimicrobial agent may be in the form of a water soluble glass containing the antimicrobial agent or compound, including those disclosed in e.g., U.S. Pat. No. 5,470,585. Still further the antimicrobial agent may be another ion-exchange type antimicrobial agent having low levels of silver ions as in, e.g., AgION XAW antimicrobial agents supplied by AgION Technologies, Inc. of Wakefield, Mass. Such additive antimicrobial and antifungal agents are known to those skilled in the art and would be added in their traditional amounts, though lesser amounts would typically be used since the primary antimicrobial agents first mentioned above are also present.

The coating compositions may also include a dopant for enhancing the initial release, and hence activity, of antimicrobial actives. Specifically, dopants provide a ready source of cations that exchange with and replace the antimicrobial silver and copper metal ions in the ion-exchange ceramic particles, thereby facilitating release and transport of these ions. Preferred dopants include, but are not limited to inorganic salts of sodium such as sodium nitrate.

Finally, the coating formulations, especially the top coat formulation in the case of multi-layered coating systems, may also contain other additives such as UV or thermal stabilizers, adhesion promoters, dyes or pigments, leveling agents, fillers and solvents. The present invention is especially suitable for use with colored coatings, i.e., those containing dyes and pigments, given the improvement in color stability resulting from the presence of the silver/copper containing antimicrobial agents. The specific additives to be use and the amount by which they can be used in the coating formulations of the present invention will depend upon the end use application and the choice of the polymer. Generally speaking, though, the selection and level of incorporation will be consistent with the directions of their manufacturers and/or known to those skilled in the art.

The antimicrobial coating compositions in accordance with the practice of the present invention may be made in accordance with any conventional method for coating preparation. Generally, the antimicrobial agent is mixed with the coating formulation during or immediately following its preparation or as a separate additive to the fully formulated coating prior to shipment and/or application. The latter is especially preferred where there is any concern that the antimicrobial additive or supplemental antimicrobial additive may adversely interact with the components of the coating composition during production and/or long term storage. In the case of powder coatings, the antimicrobial agent may be blended with the preformed powder coating particles or they may be incorporated into the pre-mix for the same, thereby dispersing the antimicrobial agent into the powder coating particles themselves.

Similarly, the coating compositions are applied by any of the methods known in the art, including spraying, brushing, rolling, printing, dipping and mold coating, powder coating, etc. The selection and thickness of the coating or coatings, in the case of multi-layered systems, can vary widely and depends upon the application requirements and limitations. For example, a high wear environment may require at thicker coating, especially one of good durability and/or wear resistance. The thickness of the coating, or the base coat in the case of multi-layered coatings, may also be a function of life of the substrate to which it is applied or, if the coating is periodically refinished or removed and replaced, the intended life of the coating itself. Generally, the thickness is the same as would be used for such coating compositions in the absence of the antimicrobial agent. Since, in practice, the antimicrobial agent may be added to commercially available coating compositions, typically the thickness and rate of application will be as recommended by the manufacturer of the same.

Similarly, where present, the top coat will have a thickness suited for the specific application, bearing in mind that the thickness is not so critical as for the base coat inasmuch as the top coat, at least in erosive coating applications, is expected to erode, thereby exposing the longer term protection of the base coat. Typically the top coat is applied so as to obtain sufficient thickness such that any surface irregularities or defects in the base coat are covered. Where the top coat also serves as a pre-applied protective layer to the underlying base coat for substrates that are coated prior to installation in their intended end-use application the coating thickness may be considerably greater to ensure that the base coat is not prematurely exposed prior to installation of the substrate. For example, many finished, coated metal parts have a release film applied to their surface to protect them from scratches and/or environmental conditions during storage and shipment. The release film is peeled off the part when put in use. In accordance with the present invention, a thicker top coat could be applied for the same purpose as the film. Costs are another factor in considering top coat thickness and composition.

Typically, the top coat formulation is more expensive than the base coat. For this reason, the thickness of the top coat is preferably no greater than that required by the application needs. Again, since, in practice, the antimicrobial agent may be added to commercially available coating compositions, the thickness and rate of application may be as recommended by the manufacturer of the same; however, again, since the top coat is not the performance coating, thinner layers are equally suitable.

When the top coat polymer is a non-hydrophilic composition, especially a skin forming non-hydrophilic composition, it is especially preferred that the thickness of the cured top coat is, at most, slightly thicker than, but preferably the same as or less than, the average diameter particle size of the antimicrobial agent and/or that a higher loading of the antimicrobial agent is employed to increase the amount of antimicrobial agent at or near the surface. Generally speaking, the thickness of the top coat is preferably less than about 20 microns and more preferably less than about 3 microns, depending upon the average particle size of the antimicrobial agent. For instance, for a top coat thickness of 3 microns, about a 3 micron or larger average diameter particle size antimicrobial agent would be used. On the other hand, if a microencapsulated antimicrobial agent is used in the top coat, for example one having a particle size of 30 microns or so, the thickness of the top coat may be up to about 30 microns. Average particle sizes of slightly less than the thickness of the top coat is possible since the distribution of particles will still provide a good number of particles in excess of the coating thickness and the coating thickness itself varies across the surface of the substrate to which it is applied. Thus, the goal is to ensure that an adequate number of particles have not skinned over so that a sufficient level of antimicrobial metal ion release is capable without having to wear away or remove the skin. In this respect one would want for at least about 30%, preferably at least about 40%, of the antimicrobial particles to have a diameter of equal to or less than the thickness of the coating. Though one could add greater quantities of antimicrobial agents whose average particle size is more than a micron or so less than the thickness of the coating, such would not be economical, especially in relatively low cost applications.

Preferred coatings for use in the practice of the present invention, whether as the sole coat or as a base or top coat, will be such that the particles do not readily settle in the coating formulation once applied. Settling has the same effect as skinning as the coating material flows over the top of the particles as they settle in the composition. Thus, coatings having a high viscosity, e.g., typical of house paint or higher, or manifesting thixotropic behavior are especially preferred. In essence, it is especially desirable that the viscosity of the coating composition be such that, following application, the coating composition cure before any significant settling has occurred, particularly where the thickness of the coating as applied to the substrate is to be greater than the particle size of the antimicrobial agent.

The coating compositions of the present invention may be applied to any of a number of surfaces or articles of manufacture, regardless of their manufacture, i.e., whether they are composed of metal, plastic, wood, glass, etc., with the selection of the specific coating matrix being dependent in part upon the surface to be coated and the conditions to which it is exposed so as to ensure sufficient surface wetting and adhesion. Such characteristics are known in the art and supplied by manufacturers of various coating materials. Suitable applications for the coatings of the present invention include, but are not limited to, building and work surfaces including walls, floors, ceilings, doors, counter tops; touch surfaces such as light switches, telephones, cutting boards, shelving, door and drawer handles and knobs, etc.; as well as various articles of manufacture including mats, containers, conveyer belts, appliances, and the like. Examples of appliance surfaces include dishwasher walls, icemakers, refrigerator shelves, showerhead faucets and the like. Other surfaces include chemical storage tanks, animal feed tanks, cooling water systems and pipes. In particular, the coating systems of the present invention are especially suited for use in food preparation and processing facilities, pharmaceutical and biotechnology related manufacturing, testing and processing facilities, and in transport vehicles and storage facilities/apparatus associated therewith including, for example, the inner walls of grain silos, rail cars, tanker trucks, bulk storage containers, etc.

The following examples are merely illustrative of the invention and are not to be deemed limiting thereof. Those skilled in the art will recognize many variations that are within the spirit of the invention and scope of the claims.

EXAMPLES 1 AND 2, COMPARATIVE EXAMPLES CE1 AND CE2

A series of coatings were prepared within and outside the scope of the present invention and exposed to various environmental conditions that they may experience in commercial use to demonstrate the unexpected color stability of the silver/copper antimicrobial agents in a two-part, 100% solids, fast curing epoxy coating system, Corro-Cote FS from Corro-Shield International of Rosemount, Ill. All formulations were prepared by adding the indicated antimicrobial agent to the resin component (part A) of the two-part epoxy composition prior to mixing the two parts. The coating was applied as a single layer (approximately 0.5 mil thick) by hand using a brush to unprimed aluminum Q panels (approx. 2" by 3.5" coupons) and allowed to cure at room temperature and room humidity (~20%). The unmodified coating, Comparative Example CE1, cured to a light gray color. Table 1 sets forth the specific formulation of each example and comparative example: amounts are presented as parts by weight.

The environmental conditions to which the panels were exposed were 24 hour room temperature, 24 hour cold water immersion, 15 minute hot water immersion (135° F.) and 5 minute steam exposure. As seen from Table 1, those compositions containing the zeolite carrier with both the silver and copper ions, Examples 1 and 2, exhibited no discoloration, similar to the control sample, Comparative Example CE1, without any antimicrobial agent, regardless of the environmental conditions. Even the presence of the minor amount of low silver content silver zeolite, XAW, in Example 2 did not affect color stability. On the other hand, comparative example CE2, which employed the AK10D grade of silver zeolite, exhibited marked discoloration in all environments.

TABLE 1

| | Example | | | |
|---|---|---|---|---|
| | Comparative Example 1 | Example 1 | Example 2 | Comparative Example 2 |
| Corro-Cote FS | 100 | 95 | 95 | 95 |
| AK10D[1] | — | — | — | 5 |
| AC10D[2] | — | 5 | 2.5 | — |
| XAW[4] | — | — | 2.5 | — |
| Silver Content | 0 | 0.175% | 0.09% | 0.25% |
| Copper Content | 0 | 0.3% | 0.15% | 0 |

TABLE 1-continued

| | Example | | | |
|---|---|---|---|---|
| | Comparative Example 1 | Example 1 | Example 2 | Comparative Example 2 |
| 24 hour bench to RT | No change | No change | No change | Turned brown |
| 24 hour cold water immersion | No change | No change | No change | Turned brown |
| 15 minute hot water immersion (135° F.) | No change | No change | No change | Brown spots |
| 5 minute steam test* | No change | No change | No change | Turned brown |

[1]AgION AK10D is a zeolite carrier having 5 wt. % silver ions
[2]AgION AJ10D is a zeolite carrier having 2.5 wt. % silver ions.
[3]AgION AC10D is a zeolite carrier having 3.5 wt. % silver and 6.0 wt. % copper ions.
[4]AgION XAW mixture of 4 parts Zinc Oxide and 1 part zeolite carrier having 0.6 wt. % silver ions
*test panels held above a beaker of boiling water
All of the tested antimicrobial agents are available from AgION Technologies, Inc. of Wakefield, MA.

EXAMPLES 3-6 AND COMPARATIVE EXAMPLES 3-6

The color stability of the use of the copper/silver antimicrobial agents was also tested in polyurethane and acrylic waxes. Here, two commercial floor finishes, Butcher's High Noon—a polyurethane fortified acrylic wax available from The Butcher Company of Sturtevant, Wis., and Zep Floor Finish—an acrylic wax available from Zep Commercial of Cartersville, Ga., were modified by incorporating 2.5% and 5.0% of AgION AC10D and AgION AK10D into separate samples. Each formulation was manually applied to clean commercial 6"×6" asbestos tiles using a brush. Three coats were applied to each tile with the modified coating allowed to cure between applications. One set of each tile was cured at room temperature and humidity (~17-20%, as indicated) and another at room temperature and high humidity (~90%). Both sets were evaluated for color change following cure. Additionally, a set of tiles cured at room temperature and humidity were buffed and then cut into 2"×2" squares and subjected to various environmental conditions and the effect on color noted. The test conditions and results are presented in Table 2. Samples of these 2"×2" squares were also evaluated for ion release by sealing their edges and soaking the same in a 0.8% sodium nitrate solution for 24 hours while rocking the sample back and forth. Ion extraction was measured by Graphite Furnace Atomic Absorption (GFAA) spectroscopy and the levels of antimicrobial ions reported were found to be adequate for providing antimicrobial activity.

As seen in Table 2, the compositions according to the practice of the present invention, Examples 3-6, did not exhibit any visibly detectable discoloration, regardless of the environmental conditions to which they were subjected. On the other hand, while no visibly detectable color change was noted in those comparative samples cured at room temperature and humidity, the comparative samples cured at room temperature and high humidity markedly discolored, turning brown. Even so, all of the comparative samples will manifest marked discoloration over time as compared to the samples made in accordance with the teaching of the present invention upon extended or long term exposure to ultraviolet light, whether natural light or artificial light, and/or humid conditions, especially high humidity as typically found in the southeastern and mid-Atlantic regions of the United States much of the year.

TABLE 2

| | Example 3 | Example 4 | Example 5 | Example 6 | Comparative Example 3 | Comparative Example 4 | Comparative Example 5 | Comparative Example 6 |
|---|---|---|---|---|---|---|---|---|
| Butchers | 95 | 97.5 | — | — | 95 | 97.5 | — | — |
| Zep | — | — | 95 | 97.2 | — | — | 95 | 97.5 |
| AK10D[1] | — | — | — | — | 5 | 2.5 | 5 | 2.5 |
| AC10D[2] | 5 | 2.5 | 5 | 2.5 | — | — | — | — |
| Silver content (wt %) | 0.175 | 0.0875 | 0.175 | 0.0875 | 0.25 | 0.125 | 0.25 | 0.125 |
| Copper content (wt %) | 0.3 | 0.15 | 0.3 | 0.15 | — | — | — | — |
| RT curing/17% Humidity | No change | No change | No change | No change | No change | No change | No change | No change |
| RT curing/90% Humidity | No change | No change | No change | No change | Turned brown | Turned Brown | Turned brown | Turned Brown |
| Tap water on windowsill* | No change | No change | No change | No change | Turned brown | — | Turned brown | — |
| 0.9% NaCl solution under lab lights* | No change | No change | No change | No change | No change | — | Turned brown | — |
| 0.9% NaCl on windowsill* | No change | No change | No change | No change | Slight browning | — | Slight browning | — |

[1] AgION AK10D is a zeolite carrier having 5 wt. % silver ions
[2] AgION AC10D is a zeolite carrier having 3.5 wt. % silver and 6.0 wt. % copper ions.
*samples were cured at RT and Room Humidity (~20%), test panels were then sprinkled with the indicated solution and the solution allowed to evaporate before color evaluation conducted

EXAMPLES 7-8 AND COMPARATIVE EXAMPLES 7-12

A series of coatings were prepared within and outside the scope of the present invention to measure color stability of the silver/copper antimicrobial agents in a gray colored two-part, 100% solids, fast curing epoxy coating systems, Corro-Cote FS, from Corro-Shield International of Rosemount, Ill. All antimicrobial formulations were prepared by adding the indicated antimicrobial agent to the resin component (part A) of the two-part epoxy composition prior to mixing the two parts. Otherwise, the coating was prepared in accordance with the manufacturer's instructions, using a 3:1 mixing ration of Part A to Part B. Each of the coatings was applied to 2 inch by 3.5 inch aluminum panels as a single layer (approximately 40-60 microns in thickness) by hand using a brush. All test panels were allowed to cure for three hours at room temperature (~70° F.) with half of the panels curing at room humidity (~30%) and the other half at approximately 80% humidity. Those test panels prepared at low humidity were placed on a windowsill for long term color stability testing.

Color stability was determined using a Minolta spectrophotometer Model No. CM3600d following cure and at 31 days. As known to those skilled in the art, this spectrophotometer measures the color shift from a given reference color or color point in the multidimensional color space. Measurements are made at three angles and the color shift, for each angle, reported as a Delta E. The greater the Delta E, the more pronounced the color shift. Typically, a Delta E of 3 or more is needed before the shift becomes visible to the naked eye. In this series of examples, color stability was established by comparing the antimicrobial coating coated panels to a standard: a test panel coated with the virgin, gray tinted Corro-Cote FS which had cured to a light gray color. For simplicity of the present application, Applicants have reported a single Delta E which represents the average of the Delta Es for each of the three angles. The results as well as the formulations are presented on Table 3.

TABLE 3

| | Ambient Humidity (~30%) | | | | High Humidity (~80%) | | | |
|---|---|---|---|---|---|---|---|---|
| | Example 7 | Comparative Example 7 | Comparative Example 8 | Comparative Example 9 | Example 8 | Comparative Example 10 | Comparative Example 11 | Comparative Example 12 |
| Corro-Cote FS epoxy | 95 | 95 | 95 | 95 | 95 | 95 | 95 | 95 |
| AC10D[1] | 5 | — | — | — | 5 | — | — | — |
| AK10D[2] | — | 5 | — | — | — | 5 | — | — |
| AJ10D[3] | — | — | 5 | — | — | — | 5 | — |
| AW10D[4] | — | — | — | 5 | — | — | — | 5 |
| Total wt % silver | 0.175 | 0.25 | 0.125 | 0.03 | 0.175 | 0.25 | 0.125 | 0.03 |
| Total wt % copper | 0.3 | — | — | — | 0.3 | — | — | — |
| Delta E (Day 1)* | 0.27 | 1.70 | 0.38 | 0.24 | 1.00 | 17.83 | 10.41 | 3.48 |
| Delta E (Day 31)* | 0.43 | 3.85 | 1.13 | 1.03 | | | | |

[1] AgION AC10D is a zeolite carrier having 3.5 wt. % silver and 6.0 wt. % copper ions.
[2] AgION AK10D is a zeolite carrier having 5 wt. % silver ions
[3] AgION AJ10D is a zeolite carrier having 2.5 wt. % silver ions.
[4] AgION AW10D is a zeolite carrier having 0.6 wt. % silver ions
*Using CleanCoat FS floor coating w/o antimicrobial as the standard As seen in Table 3 and FIG. 1, those test panels employing the silver/copper antimicrobial manifested markedly less discoloration as compared to those employing the silver antimicrobial free of copper ions, especially in high humidity applications. Though the data suggests that less discoloration occurred with Comparative Example 9 as compared to Example 7 under low humidity conditions, there was no visible difference to speak of. Furthermore, but for one anomalous data point (the Example 7 Delta Es were 0.26, 0.32 and 0.23 and the CE9 Delta Es were 0.24, 0.24, and 0.24), the results were for all practical purposes the same. While the shift in color was not so marked upon cure, after only 31 days all comparative examples prepared at room temperature and low humidity demonstrated significant Delta Es, a factor indicative of their long term color instability. Indeed, in just that short time, Comparative Example CE9 manifested sufficient color change to be visible to the naked eye. While the color shifts in Comparative Examples CE7 and CE8 were not visibly detectable, they are nonetheless significant and representative of the marked color shift to be seen as the samples continue to age. On the other hand, only a negligible color shift was noted for Example 7: certainly nothing close to being visible to the naked eye. While it is expected that this slight color shift will continue over time, this color shift will be of minimal consequence, particularly as compared to the coatings of the comparative examples.

Table 3 also shows the impact cure at higher humidity has upon color shift. As seen all comparative examples, CE10-12, manifested marked and visible color shift as compared to the inventive coating of the present application. This is especially surprising inasmuch as Comparative Examples 11 and 12 have less silver, markedly less (about one-fifth) in the case of the latter, than the example in accordance with the present invention, Example 8.

EXAMPLES 9-12 AND COMPARATIVE EXAMPLE 13

A further set of examples and comparative examples were prepared as described in the preceding example, this time employing a white version of the aforementioned Corro-Cote FS. All samples were allowed to cure at room temperature and humidity and then set on a shelf where they exposed to both natural and artificial light for one year. The formulations and discoloration data (the average of the three data points) are presented in Table 4.

TABLE 4

| | Example | | | | |
|---|---|---|---|---|---|
| | Example 9 | Example 10 | Example 11 | Example 12 | Comparative Example 13 |
| Corro-Cote FS - white | 95 | 95 | 95 | 90 | 95 |
| AC10D[1] | 5 | 2.5 | — | — | — |
| XAC[2] | — | — | 5 | 10 | — |
| XAW[3] | — | 2.5 | — | — | — |
| AK10D[4] | — | — | — | — | 5 |
| Delta E | 2.87 | 2.59 | 4.38 | 7.87 | 42.98 |

[1] AgION AC10D is a zeolite carrier having 3.5 wt. % silver and 6.0 wt. % copper ions.
[2] AgION XAC is a blend of 4 parts zinc oxide and 1 part AC10D.
[3] AgION XAW mixture of 4 parts Zinc Oxide and 1 part zeolite carrier having 0.6 wt. % silver ions
[4] AgION AK10D is a zeolite carrier having 5 wt. % silver ions As seen in Table 4, although the spectrophotometer was able to detect some color change in the coatings in accordance with the practice of the present invention after one year, the change was minimal and not visible to the naked eye. While a minor color shift was noted after one year with those examples employing the silver-copper zeolite in combination with high loadings of Zinc Oxide (4% in Example 11 and 8% in Example 12 as compared to 2% in Example 10), the shift is still markedly less than that color shift found with the silver zeolite alone in Comparative Example 13. Thus, in use, care should be taken to avoid adding high levels of other constituents, including other antimicrobial agents such as zinc oxide and/or silver zeolite, especially constituents which may affect the color of the coating into which it is being incorporated. Still, as noted, the color shift attributable to the other additives pales in comparison to the discoloration of Comparative Example 13 which had turned to a dark caramel color.

Perhaps the most interesting phenomenon that manifested itself with the use of the silver and copper ion containing zeolites, especially the AgION AC10D, in the white coating was an apparent enhancement of the whiteness or brilliance of the white coating. In essence, the presence of the silver/copper zeolite rendered the coating "super white" in appearance. Thus, here, the color shift evidenced by the Delta E value, at least as it pertains to the silver/copper zeolites, is almost a misnomer, since the color shift, once it achieves the level detectable by the naked eye, actually reflects a beneficial change to a more brilliant white. Furthermore, it is believed that the presence of the silver/copper zeolite may also counteract or give the appearance of counteracting the loss in color or vibrancy of the color due to the natural aging and, consequently fading, of the white Corro-Cote FS coating itself. These beneficial effects, however, are limited as employing higher and higher levels of copper in a white colored coating will have a tendency to manifest a bluish hue to a light blue coloration in the white coating depending upon the amount of copper present. Regardless, as seen, the presence of the copper/silver zeolite manifests improved color stability as compared to other antimicrobial coatings.

Although the present invention has been described with respect to the foregoing specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles.

We claim:

1. A substantially color stable antimicrobial coating system comprising an epoxy resin-based or wax-based coating composition and from about 1 wt. % to about 30 wt. % based on the total solids content of the coating composition of an antimicrobial metal-ion containing, ion-exchange type inorganic antimicrobial agent said antimicrobial agent comprising from about 0.1 wt. % to about 25 wt. % silver ions and 0.1 wt. % to about 25 wt. % copper ions, based on the weight of the antimicrobial agent, and wherein the weight ratio of the silver ions to the copper ions is from about 1:10 to about 10:1.

2. The antimicrobial coating system of claim 1 wherein the antimicrobial agent is present in an amount of from about 2 wt. % to about 25 wt. % based on the total solids.

3. The antimicrobial coating system of claim 1 wherein the antimicrobial agent is present in an amount of from about 4 wt. % to about 20 wt. % based on the total solids.

4. The antimicrobial coating system of claim 1 wherein the antimicrobial agent comprises from about 0.3 wt. % to about 15 wt. % silver ions and 0.3 wt. % to about 15 wt. % copper ions, based on the weight of the antimicrobial agent, and wherein the weight ratio of the silver ions to the capper ions is from about 1:5 to about 5:1.

5. The antimicrobial coating system of claim 1 wherein the antimicrobial agent comprises from about 0.3 wt. % to about 15 wt. % silver ions and 0.3 wt. % to about 15 wt. % copper ions, based on the weight of the antimicrobial agent, and wherein the weight ratio of the silver Ions to the copper ions is from about 1:2.5 to about 2.5:1.

6. The antimicrobial coating system of claim 1 wherein the antimicrobial metal ion-containing inorganic antimicrobial agent comprises ion-exchange type ceramic particles.

7. The antimicrobial coating system of claim 6 wherein the ceramic particles are selected from the group consisting of zeolites, hydroxyapatites, and zirconium phosphates.

8. The antimicrobial coating system of claim 6 wherein the ceramic particles are zeolite.

9. The antimicrobial coating system of claim 1 comprising a single coating composition containing the antimicrobial agent.

10. The antimicrobial coating system of claim 1 comprising at least two coating compositions, an epoxy resin-based or wax-based base layer coating composition and a top layer coating composition, wherein at least the base layer coating composition comprises the antimicrobial agent.

11. The antimicrobial coating system of claim 10 wherein both coating compositions comprise the antimicrobial agent.

12. The antimicrobial coating system of claim 11 wherein the base layer coating composition, when cured, is a non-hydrophilic material and the top layer coating composition, when cured, is a (a) hydrophilic material or (b) a non-hydrophilic material that is either (i) skin forming, provided that the thickness of the top coat is such that an adequate number of particles of the antimicrobial agent are not skinned over so as to preclude the presence at the surface of the top coat of an antimicrobially effective amount of the antimicrobial agent, or (ii) non skin forming with respect to the antimicrobial agent.

13. The antimicrobial coating system of claim 12 wherein the top layer coating composition cures to a hydrophilic material that is readily eroded.

14. The antimicrobial coating system of claim 13 wherein the cured hydrophilic material selected from the group consisting of poly(alkylene ether) esters, polyacrylates, polymethacrylates, polyurethanes, polyamides, polyacrylamides, polymethacrylamides, polyvinylpyrrolidinones, polyureas, polysaccharides, polyvinylacetates, polyvinylalcohols, copolymers of the foregoing, copolymers having a substantial presence of hydrophilic monomers used in the foregoing and blends of any two or more of the foregoing.

15. The antimicrobial coating system of claim 1 wherein the coating composition is curable thermoset composition.

16. The antimicrobial coating system of claim 1 further comprising a second antimicrobial agent which is independently selected from the group consisting of metal salts, antimicrobial metal or metal ion containing water soluble glasses, ion-exchange type antimicrobial metal agents and combinations thereof provided that the selected antimicrobial agent at the level used, does not markedly effect discoloration in the cured coating.

17. The antimicrobial coating system of claim 1 wherein the coating composition is an acrylic wax-based coating.

18. The antimicrobial coating system of claim 1 wherein the coating composition is an urethane or polyurethane wax-based coating.

19. The antimicrobial coating system of claim 1 wherein the coating composition is an epoxy novalak resin.

20. The antimicrobial coating system of claim 1 wherein the coating composition is an epoxy polyester resin.

* * * * *